(12) United States Patent
Yu et al.

(10) Patent No.: US 12,697,054 B2
(45) Date of Patent: Aug. 4, 2026

---

(54) BLOOD COLLECTION TUBE SORTING AND CENTRIFUGAL BALANCING DEVICE

(71) Applicant: Fuwai Hospital, Beijing (CN)

(72) Inventors: Jinxing Yu, Beijing (CN); Yang Zhang, Beijing (CN); Kai Cui, Beijing (CN); Zhou Zhou, Beijing (CN); Yahui Lin, Beijing (CN)

(73) Assignee: Fuwai Hospital, Beijing (CN)

( * ) Notice: Subject to any disclaimer, the term of this patent is extended or adjusted under 35 U.S.C. 154(b) by 724 days.

(21) Appl. No.: 18/326,008

(22) Filed: May 31, 2023

(65) Prior Publication Data

US 2023/0380737 A1 Nov. 30, 2023

(30) Foreign Application Priority Data

May 31, 2022 (CN) .......................... 202210612746.2
May 31, 2022 (CN) .......................... 202221342477.4

(51) Int. Cl.
*A61B 5/15* (2006.01)

(52) U.S. Cl.
CPC .. *A61B 5/150015* (2013.01); *A61B 5/150763* (2013.01); *A61B 5/150206* (2013.01)

(58) Field of Classification Search
CPC ............. G01N 35/04; G01N 35/00722; G01N 2035/0406; G01N 2035/00495; A61B 5/150015; A61B 5/150206; A61B 5/150343; A61B 5/150763
See application file for complete search history.

(56) References Cited

U.S. PATENT DOCUMENTS

2009/0054222 A1* 2/2009 Zhang ..................... C40B 30/10
                                                              901/6
2009/0318276 A1* 12/2009 Miller ...................... B04B 5/10
                                                              494/20

* cited by examiner

*Primary Examiner* — Robert J Eom

(57) ABSTRACT

Provided is a blood collection tube sorting and centrifugal balancing device including a body frame. A vacuum blood collection tube mechanism, a centrifugal balancing tube mechanism, a sorting mechanism, a scanning identification mechanism, a test tube transporting mechanism, and a collection box are arranged on the body frame. The vacuum blood collection tube mechanism and the centrifugal balancing tube mechanism are parallelly arranged on an upper part of the body frame. The scanning identification mechanism is connected to the vacuum blood collection tube mechanism. The sorting mechanism is connected to the vacuum blood collection tube mechanism and the centrifugal balancing tube mechanism at two ends of the sorting mechanism, respectively. The test tube transporting mechanism is connected to the centrifugal balancing tube mechanism. The collection box is disposed in a middle part of the body frame and located directly below the vacuum blood collection tube mechanism.

10 Claims, 7 Drawing Sheets

BLOOD COLLECTION TUBE SORTING AND CENTRIFUGAL BALANCING DEVICE

CROSS-REFERENCE TO RELATED APPLICATIONS

This application claims priority to Chinese Patent Applications No. 202210612746.2 filed on May 31, 2022, and No. 202221342477.4 filed on May 31, 2022, the entire disclosures of which are incorporated herein by reference.

FIELD

The present disclosure relates to the technical field of common device in medical laboratories, and more particularly, to a blood collection tube sorting and centrifugal balancing device.

BACKGROUND

Medical clinical examination has been rapidly developed, especially the use of vacuum blood collection tubes to collect and examine blood specimens has constituted a basic mode of an automatic examination flow line, and realized automation of collection, transportation, centrifugation, examination, and storage of the blood specimens by using the vacuum blood collection tubes. However, in practical application, due to the different examination items, requirements for the blood collection tubes are different from each other, and there are examination items with or without centrifugation.

Centrifuges is also required that quantity and quality of blood collection tubes placed into the centrifuges should be relatively balanced, while blood collection tubes with different examination requirements will be delivered to the automatic examination flow line at the same time. An amount of blood collection tubes to be centrifuged cannot be balanced, which may cause the centrifuges to unable to work. Human intervention is needed to solve such problems. Due to this phenomenon, in night shift, when the automatic examination flow line is unattended, the flow line may be blocked, so that the examination cannot be normally carried out. However, the night shift is often in an emergency treatment high-incidence period.

It is therefore of great importance to develop a device that can solve the above-mentioned defects.

SUMMARY

The present disclosure provides a blood collection tube sorting and centrifugal balancing device, which can carry out sorting and balancing operations, so that an automatic examination flow line can run smoothly under an unattended condition.

In order to achieve the above purpose, the present disclosure adopts the following technical solution.

Embodiments of the present disclosure provides a blood collection tube sorting and centrifugal balancing device including a body frame. A vacuum blood collection tube mechanism, a centrifugal balancing tube mechanism, a sorting mechanism, a scanning identification mechanism, a test tube transporting mechanism, and a collection box are arranged on the body frame. The vacuum blood collection tube mechanism and the centrifugal balancing tube mechanism are parallelly arranged on an upper part of the body frame. A vacuum blood collection tube is placeable into the vacuum blood collection tube mechanism, and the vacuum blood collection tube mechanism is configured to extract the vacuum blood collection tube onto the scanning identification mechanism. A centrifugal balancing tube is placeable into the centrifugal balancing tube mechanism, and the centrifugal balancing tube mechanism is configured to extract the centrifugal balancing tube onto the test tube transporting mechanism.

The sorting mechanism, the scanning identification mechanism, and the test tube transporting mechanism are arranged between the vacuum blood collection tube mechanism and the centrifugal balancing tube mechanism. The scanning identification mechanism and the test tube transporting mechanism are parallelly arranged below the sorting mechanism. The scanning identification mechanism is connected to the vacuum blood collection tube mechanism and is configured to scan and identify a label of the vacuum blood collection tube extracted by the vacuum blood collection tube mechanism. The sorting mechanism is connected to the vacuum blood collection tube mechanism and the centrifugal balancing tube mechanism at two ends of the sorting mechanism, respectively, and configured to sort the vacuum blood collection tube extracted onto the scanning identification mechanism by the vacuum blood collection tube mechanism. The test tube transporting mechanism is connected to the centrifugal balancing tube mechanism, and configured to transport the vacuum blood collection tube with correct label information sorted out by the sorting mechanism and the centrifugal balancing tube extracted by the centrifugal balancing tube mechanism to a subsequent detection flow line for processing.

The collection box is disposed in a middle part of the body frame and located directly below the vacuum blood collection tube mechanism, and configured to collect the vacuum blood collection tube with incorrect label information sorted out by the sorting mechanism.

In some embodiments of the present disclosure, the vacuum blood collection tube mechanism includes a vacuum tube conveying mechanism, a vacuum tube extraction mechanism, and a vacuum tube hopper. The vacuum tube hopper is disposed on the vacuum tube conveying mechanism, and the vacuum blood collection tube is placeable into the vacuum tube hopper. The vacuum tube conveying mechanism and the vacuum tube extraction mechanism are parallelly arranged on the collection box. The vacuum tube conveying mechanism is configured to convey the vacuum blood collection tube in the vacuum tube hopper to the vacuum tube extraction mechanism. The vacuum tube extraction mechanism is configured to extract the vacuum blood collection tube conveyed by the vacuum tube conveying mechanism to the scanning identification mechanism.

In some embodiments of the present disclosure, the vacuum tube conveying mechanism includes a vacuum tube conveying rack, a vacuum tube conveying motor, a vacuum tube driving shaft, and a vacuum tube conveying belt. The vacuum tube conveying rack is disposed across the collection box. The vacuum tube driving shaft is disposed at two ends of the vacuum tube conveying rack. The vacuum tube conveying motor is disposed at one end of the vacuum tube conveying rack and connected to the vacuum tube driving shaft. The vacuum tube conveying belt is disposed on the vacuum tube driving shaft. The vacuum tube conveying motor is configured to drive the vacuum tube driving shaft to drive the vacuum tube conveying belt to convey the vacuum blood collection tube onto the vacuum tube extracting mechanism.

In some embodiments of the present disclosure, the vacuum tube extracting mechanism includes a vacuum tube extracting rack, a vacuum tube extracting motor, a vacuum tube extracting rotation shaft, a vacuum tube extracting belt, a vacuum tube transition block, a vacuum tube extracting block, and a vacuum tube guide block. The vacuum tube extracting rack is vertically disposed on the collection box. The vacuum tube extracting rotation shaft is disposed at two ends of the vacuum tube extracting rack. The vacuum tube extracting motor is disposed at a lower end of the vacuum tube extracting rack and connected to the vacuum tube extracting rotation shaft. The vacuum tube extracting belt is disposed on the vacuum tube extracting rotation shaft. The vacuum tube transition block is disposed on the vacuum tube extracting rack and located at a same level as the vacuum tube conveying mechanism. The vacuum tube extracting block is disposed on the vacuum tube extracting belt. The vacuum tube guide block is disposed at an upper end of the vacuum tube extracting rack. The vacuum tube extracting motor is configured to drive the vacuum tube extracting rotation shaft to drive the vacuum tube extracting block to lift to extract the vacuum blood collection tube onto the scanning identification mechanism.

In some embodiments of the present disclosure, the scanning identification mechanism includes a scanning rack, a scanning motor, scanning dual rollers, and a scanner. The scanning rack is disposed on the vacuum tube extracting rack. The scanning dual rollers are disposed on a top of the scanning rack. The scanning motor is disposed on the scanning rack, and connected to the scanning dual rollers to drive the scanning dual rollers. The scanner is disposed on a bottom of the scanning rack and corresponding to a gap between the scanning dual rollers.

In some embodiments of the present disclosure, the test tube transporting mechanism includes a transporting rack, a transporting motor, a transporting driving wheel, a transporting belt, and a transporting guide block. The transporting rack is connected to the centrifugal balancing tube mechanism. The transporting driving wheel is disposed at two ends of the transporting rack. The transporting motor disposed at one end of the transporting rack, and connected to the transporting driving wheel to drive the transporting driving wheel. The transporting belt is disposed on the transporting driving wheel to receive and transport the vacuum blood collection tube conveyed from the sorting mechanism or the centrifugal balancing tube conveyed from the centrifugal balancing tube mechanism. The transporting guide block is disposed at one end of the transporting rack and configured to accurately place the vacuum blood collection tube or the centrifugal balancing tube on the transporting belt onto the subsequent detection flow line.

In some embodiments of the present disclosure, the centrifugal balancing tube mechanism includes a balancing tube conveying mechanism, a balancing tube extracting mechanism, and a balancing tube hopper. The balancing tube hopper is disposed on the balancing tube conveying mechanism, and the centrifugal balancing tube is placeable in the balancing tube hopper. The balancing tube conveying mechanism and the balancing tube extracting mechanism are parallelly arranged on the body frame. The balancing tube conveying mechanism is configured to convey the centrifugal balancing tube in the balancing tube hopper onto the balancing tube extracting mechanism. The balancing tube extracting mechanism is configured to extract the centrifugal balancing tube conveyed by the balancing tube conveying mechanism onto the test tube transporting mechanism.

In some embodiments of the present disclosure, the balancing tube conveying mechanism includes a balancing tube conveying rack, a balancing tube conveying motor, a balancing tube transmission shaft, and a balancing tube conveying belt. The balancing tube conveying rack is disposed across the body frame. The balancing tube transmission shaft is disposed at two ends of the balancing tube conveying rack. The balancing tube conveying motor is disposed at one end of the balancing tube conveying rack, and connected to the balancing tube transmission shaft to drive the balancing tube transmission shaft. The balancing tube conveying belt is disposed on the balancing tube transmission shaft to convey the centrifugal balancing tube to the balancing tube extracting mechanism.

In some embodiments of the present disclosure, the balancing tube extracting mechanism includes a balancing tube extracting rack, a balancing tube extracting motor, a balancing tube extracting rotation shaft, a balancing tube extracting belt, a balancing tube transition block, a balancing tube extracting block, a balancing tube guide block, and a turning plate. The balancing tube extracting rack is vertically disposed on the body frame. The balancing tube extracting rotation shaft is disposed at two ends of the balancing tube extracting rack. The balancing tube extracting motor is disposed at a lower end of the balancing tube extracting rack, and connected to the balancing tube extracting rotation shaft to drive the balancing tube extracting rotation shaft. The balancing tube extracting belt is disposed on the balancing tube extracting rotation shaft. The balancing tube transition block is disposed on the balancing tube extracting rack and located at a same level as the balancing tube conveying mechanism. The balancing tube extracting block is disposed on the balancing tube extracting belt. The balancing tube guide block and the turning plate are parallelly arranged at an upper end of the vacuum tube extracting rack. The turning plate is configured to guide the centrifugal balancing tube from the balancing tube guide block to the test tube transporting mechanism or guide the vacuum blood collection tube with incorrect label information sorted out by the sorting mechanism to the collection box.

In some embodiments of the present disclosure, the sorting mechanism includes a sorting mounting plate, a sorting motor, a sorting slide rail module, a sorting transmission gear, a sorting transmission rack, and a sorting frame. The sorting mounting plate is connected to the vacuum blood collection tube mechanism and the centrifugal balancing tube mechanism at two ends of the sorting mounting plate, respectively. The sorting motor is disposed on the sorting mounting plate. The sorting slide rail module is disposed on the sorting mounting plate. The sorting transmission gear is connected to the sorting motor. The sorting transmission rack is disposed on the sorting slide rail module and engaged with the sorting transmission gear. The sorting frame is disposed on the sorting slide rail module. The sorting motor is configured to drive the sorting transmission gear to drive the sorting transmission rack and the sorting frame to move along the sorting slide rail module.

Compared with the related art, the present disclosure has advantages that the vacuum blood collection tube can be identified and sorted by the scanning identification mechanism and the sorting mechanism, and the vacuum blood collection tube with incorrect label information can be removed. Thus, it is possible to avoid errors in subsequent operations. Through the centrifugal balancing tube mechanism, the centrifugal balancing tube can be matched with the vacuum blood collection tube entering the next process. Missing or over-matching will not occur in this fully automatic matching mode. The present disclosure provides an automatic device for pre-storing and centrifugal balancing for the automatic examination flow line, so that the automatic examination flow line can run smoothly under the unattended condition.

DETAILED DESCRIPTION

Technical solutions according to embodiments of the present disclosure will be fully and clearly described below in combination with accompanying drawings of the embodiments of the present disclosure. Obviously, the embodiments described below are merely a part, rather than all of the embodiments of the present disclosure.

It should be noted that when a component/part is "disposed" on another component/part, it can be directly disposed on the other component/part or there can also be an intermediate component/part therebetween. When a component/part is "connected/coupled" to another component/part, it may be directly connected/coupled to the other component/part or there can also be an intermediate component/part therebetween. The term "connection/coupling" as used herein may include an electrical and/or mechanical-physical connection/coupling. As used herein, the term "including/comprising" refers to the presence of a feature, step or component/part, but does not exclude the presence or addition of one or more other features, steps, or components/parts. The term "and/or" as used herein includes any and all combinations of one or more related listed items.

Unless otherwise defined, all technical and scientific terms used herein have the same meaning as would normally be understood by those skilled in the related art of the present disclosure. The terms used herein is merely for the purpose of describing specific embodiments and is not intended to limit the present disclosure.

Figure 1:
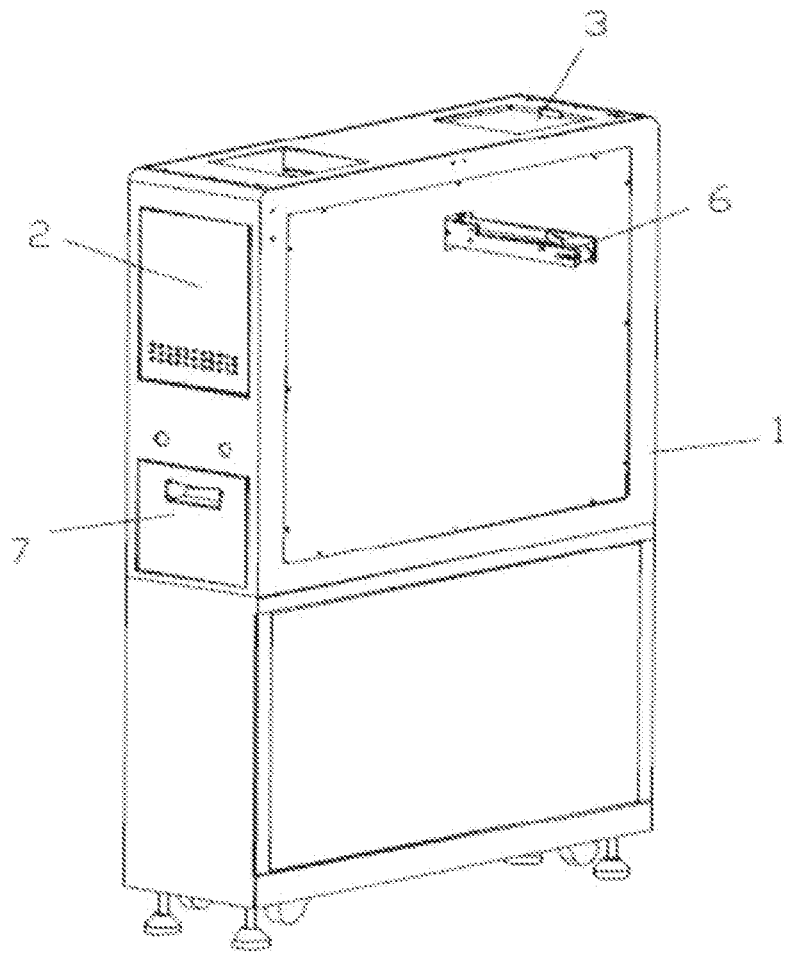
FIG. 1 is a schematic view of an overall structure according to an embodiment of the present disclosure.
Figure 2:
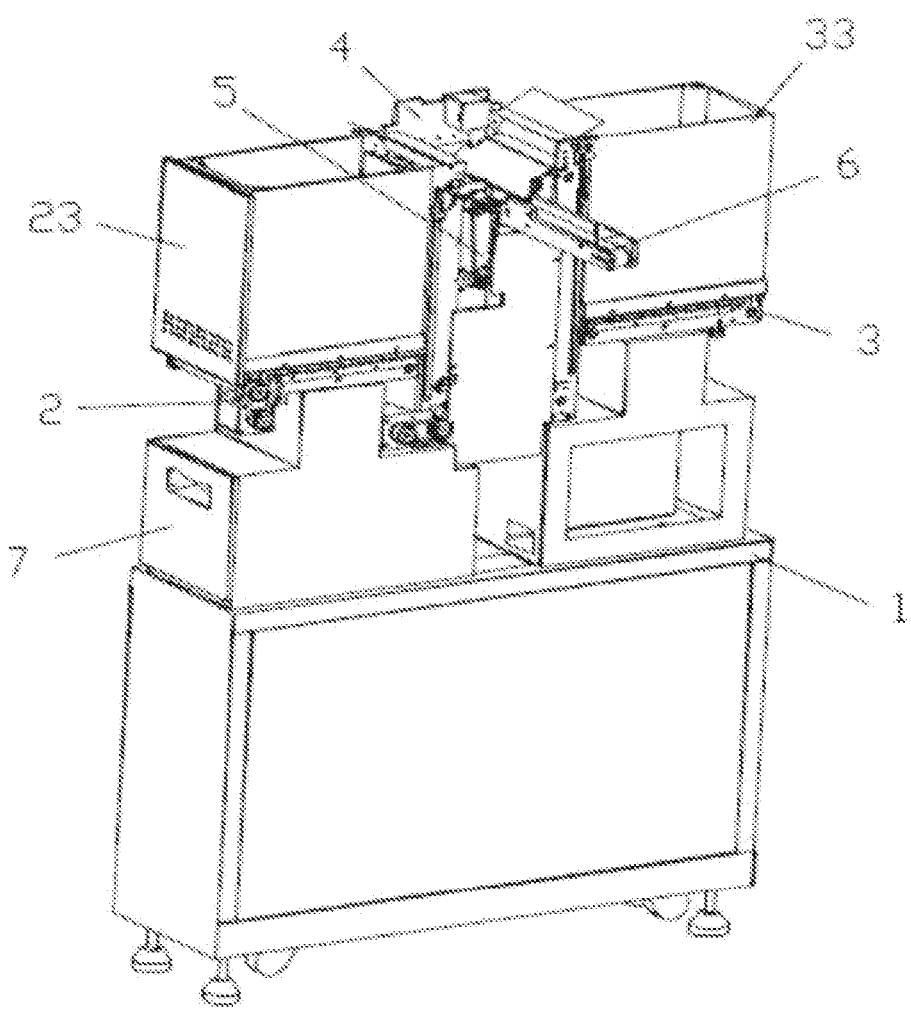
FIG. 2 is a schematic view of an internal structure according to an embodiment of the present disclosure.

Referring to FIG. 1 and FIG. 2, provided is a blood collection tube sorting and centrifugal balancing device, including a body frame 1, a vacuum blood collection tube mechanism 2, a centrifugal balancing tube mechanism 3, a sorting mechanism 4, a scanning identification mechanism 5, a test tube transporting mechanism 6, and a collection box 7 that are arranged on the body frame 1. The vacuum blood collection tube mechanism 2 and the centrifugal balancing tube mechanism 3 are parallelly arranged on an upper part of the body frame 1. A vacuum blood collection tube is placeable into the vacuum blood collection tube mechanism 2. The vacuum blood collection tube mechanism 2 is configured to extract the vacuum blood collection tube onto the scanning identification mechanism 5. The centrifugal balancing tube is placeable into the centrifugal balancing tube mechanism. The centrifugal balancing tube mechanism 3 is configured to extract the centrifugal balancing tube onto the test tube transporting mechanism 6. The sorting mechanism 4, the scanning identification mechanism 5, and the test tube transporting mechanism 6 are arranged between the vacuum blood collection tube mechanism 2 and the centrifugal balancing tube mechanism 3. The scanning identification mechanism 5 and the test tube transporting mechanism 6 are parallelly arranged below the sorting mechanism 4. The scanning identification mechanism 5 is connected to the vacuum blood collection tube mechanism 2 to scan and identify a label of the vacuum blood collection tube extracted by the vacuum blood collection tube mechanism 2. The sorting mechanism 4 is connected to the vacuum blood collection tube mechanism 2 and the centrifugal balancing tube mechanism 3 at two ends of the sorting mechanism 4, respectively, to sort the vacuum blood collection tube extracted to the scanning identification mechanism 5 by the vacuum blood collection tube mechanism 2. The test tube transporting mechanism 6 is connected to the centrifugal balancing tube mechanism 3 to transport the vacuum blood collection tube with correct label information sorted out by the sorting mechanism 4 and the centrifugal balancing tube extracted by the centrifugal balancing tube mechanism 3 to a subsequent detection flow line for processing. The collection box 7 is disposed in a middle part of the body frame 1 and located directly below the vacuum blood collection tube mechanism 2, to collect the vacuum blood collection tube with incorrect label information sorted out by the sorting mechanism 4.

In operation, the vacuum blood collection tube and the centrifugal balancing tube are placed into the vacuum blood collection tube mechanism 2 and the centrifugal balancing tube mechanism 3. The vacuum blood collection tube is extracted onto the scanning identification mechanism 5 by the vacuum blood collection tube mechanism 2, and then label information on the vacuum blood collection tube is scanned and identified by the scanning identification mechanism 5. The vacuum blood collection tubes with incorrect label information is sorted into the collection box by the sorting mechanism 4, and the vacuum blood collection tube with correct label information is sorted onto the test tube transporting mechanism 6 to be delivered for next process. The centrifugal balancing tube mechanism 3 can match corresponding amount of the centrifugal balancing tubes onto the test tube transporting mechanism 6 based on an amount of the vacuum blood collection tubes transported by the test tube transporting mechanism 6 for delivering to the next process. Therefore, it is possible to ensure that the amount of vacuum blood collection tubes can correspond to the amount of the centrifugal balancing tubes, so that the whole flow line can be continuously operated under an unattended condition.

Figure 3:
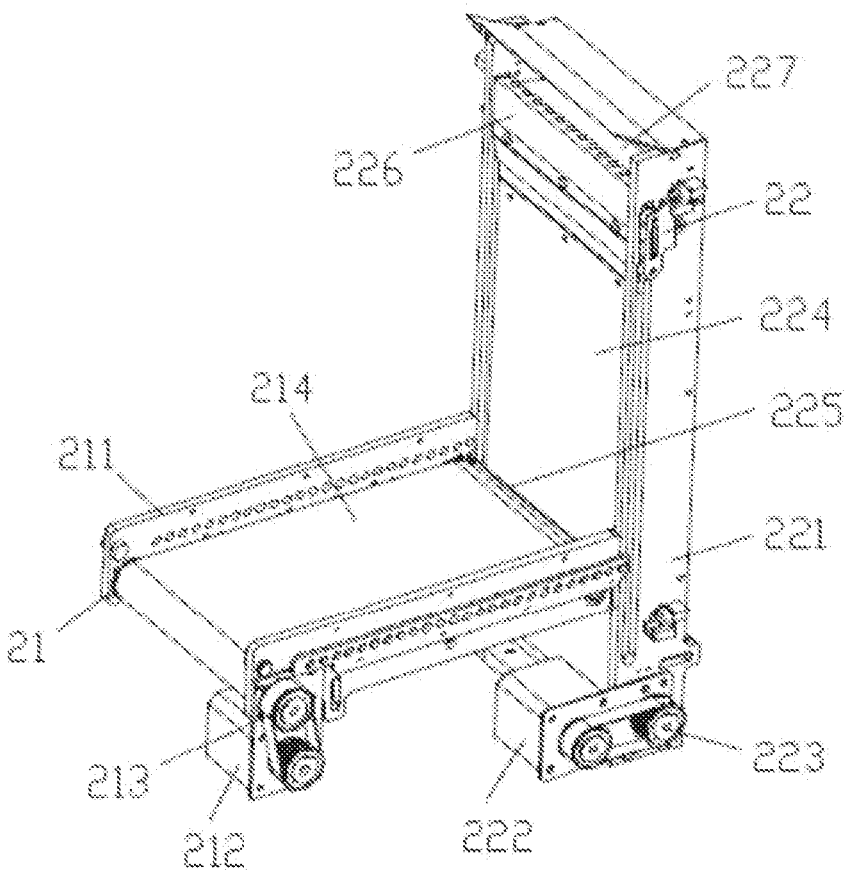
FIG. 3 is an internal schematic view of a vacuum blood collection tube mechanism according to an embodiment of the present disclosure.

Referring to FIG. 3, the vacuum blood collection tube mechanism 2 includes a vacuum tube conveying mechanism 21, a vacuum tube extraction mechanism 22, and a vacuum tube hopper 23. The vacuum tube hopper 23 is disposed on the vacuum tube conveying mechanism 21, and the vacuum blood collection tube is placeable into the vacuum tube hopper 23. The vacuum tube conveying mechanism 21 and the vacuum tube extraction mechanism 22 are parallelly arranged above the collection box. The vacuum tube conveying mechanism 21 is configured to convey the vacuum blood collection tube in the vacuum tube hopper 23 onto the vacuum tube extraction mechanism 22. The vacuum tube extraction mechanism 22 is configured to extract the vacuum blood collection tube conveyed by the vacuum tube conveying mechanism 21 onto the scanning identification mechanism 5.

The vacuum tube conveying mechanism 21 includes a vacuum tube conveying rack 211, a vacuum tube conveying motor 212, a vacuum tube driving shaft 213, and a vacuum tube conveying belt 214. The vacuum tube conveying rack 211 is disposed across the collection box 7. The vacuum tube driving shaft 213 is disposed at two ends of the vacuum tube conveying rack 211. The vacuum tube conveying motor 212 is disposed at one end of the vacuum tube conveying rack 211 and connected to the vacuum tube driving shaft 213. The vacuum tube conveying belt 214 is disposed on the vacuum tube driving shaft 213. In operation, the vacuum tube conveying motor 212 can drive the vacuum tube driving shaft 213 to drive the vacuum tube conveying belt to convey the vacuum blood collection tube onto the vacuum tube extracting mechanism 22.

The vacuum tube extracting mechanism 22 includes a vacuum tube extracting rack 221, a vacuum tube extracting motor 222, a vacuum tube extracting rotation shaft 223, a vacuum tube extracting belt 224, a vacuum tube transition block 225, a vacuum tube extracting block 226, and a vacuum tube guide block 227. The vacuum tube extracting rack 221 vertically disposed on the collection box 7. The vacuum tube extracting rotation shaft 223 is disposed at two ends of the vacuum tube extracting rack 221. The vacuum tube extracting motor 222 is disposed at a lower end of the vacuum tube extracting rack 221 and connected to the vacuum tube extracting rotation shaft 223. The vacuum tube extracting belt 224 is disposed on the vacuum tube extracting rotation shaft 223. The vacuum tube transition block 225 is disposed on the vacuum tube extracting rack 221 and located at a same level as the vacuum tube conveying mechanism 21. The vacuum tube extracting block 226 is disposed on the vacuum tube extracting belt 224. The vacuum tube guide block 227 is disposed at an upper end of the vacuum tube extracting rack 221. In operation, the vacuum tube conveying mechanism 21 can convey the vacuum blood collection tube onto the vacuum tube transition block 225. The vacuum tube extracting motor 222 can drive the vacuum tube extracting rotation shaft 223 to drive the vacuum tube extracting block 226 to lift to extract the vacuum blood collection tube on the vacuum tube transition block 225 onto the vacuum tube guide block 227, and then the vacuum blood collection tube is dropped onto the scanning identification mechanism 5.

Figure 6:
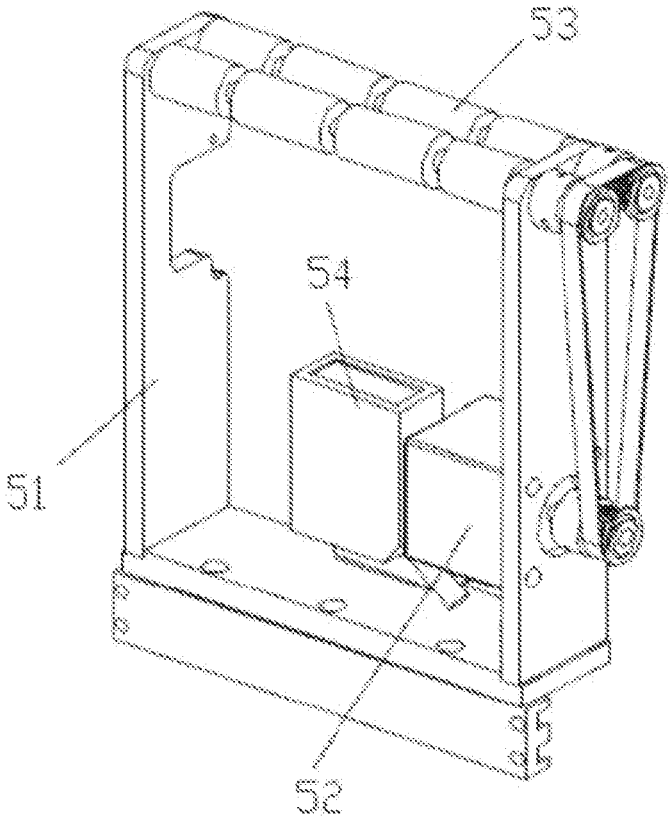
FIG. 6 is a schematic structural view of a scanning identification mechanism according to the present disclosure.

Referring to FIG. 6, the scanning identification mechanism 5 includes a scanning rack 51, a scanning motor 52, scanning dual rollers 53, and a scanner 54. The scanning rack 51 is disposed on the vacuum tube extracting rack 221. The scanning dual rollers 53 are disposed on a top of the scanning rack 51. The scanning motor 52 is disposed on the scanning rack 51, and connected to the scanning dual rollers 53 to drive the scanning dual rollers 52. The scanner 54 is disposed on a bottom of the scanning rack 51 and located at a position corresponding to a gap between the scanning dual rollers 53. In operation, the scanning motor 52 can drive the scanning double rollers 53 to roll the vacuum blood collection tube, and the scanner 54 can scan and identify the label on the vacuum blood collection tube by scanning the gap between the scanning double rollers 53, to determine whether the vacuum blood collection tube is a centrifuge tube or a non-centrifuge tube.

Figure 7:
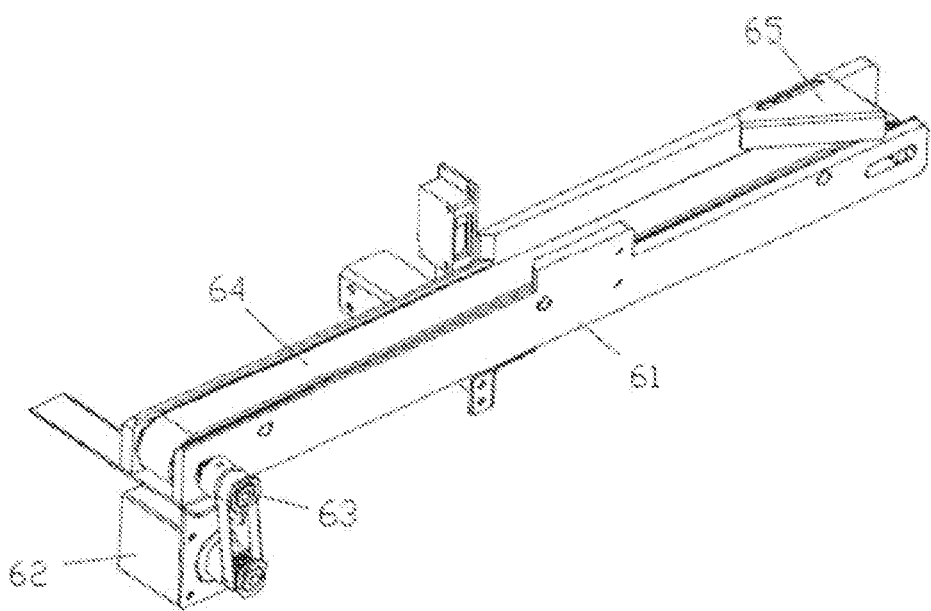
FIG. 7 is a schematic structural view of a test tube transporting mechanism of the present disclosure.

Referring to FIG. 7, the test tube transporting mechanism 6 includes a transporting rack 61, a transporting motor 62, a transporting driving wheel 63, a transporting belt 64, and a transporting guide block 65. The transporting rack 61 is connected to the centrifugal balancing tube mechanism 3. The transporting driving wheel 63 is disposed at two ends of the transporting rack 61. The transporting motor 62 is disposed at one end of the transporting rack 61, and connected to the transporting driving wheel 63 to drive the transporting driving wheel 63. The transporting belt 64 is disposed on the transporting driving wheel 63 to receive and transport the vacuum blood collection tube conveyed from the sorting mechanism 4 or the centrifugal balancing tube conveyed from the centrifugal balancing tube mechanism 3. The transporting guide block 65 is disposed at an end of the conveying rack 61 to accurately place the vacuum blood collection tube or the centrifugal balancing tube on the transporting belt 64 onto the subsequent detection flow line.

Figure 4:
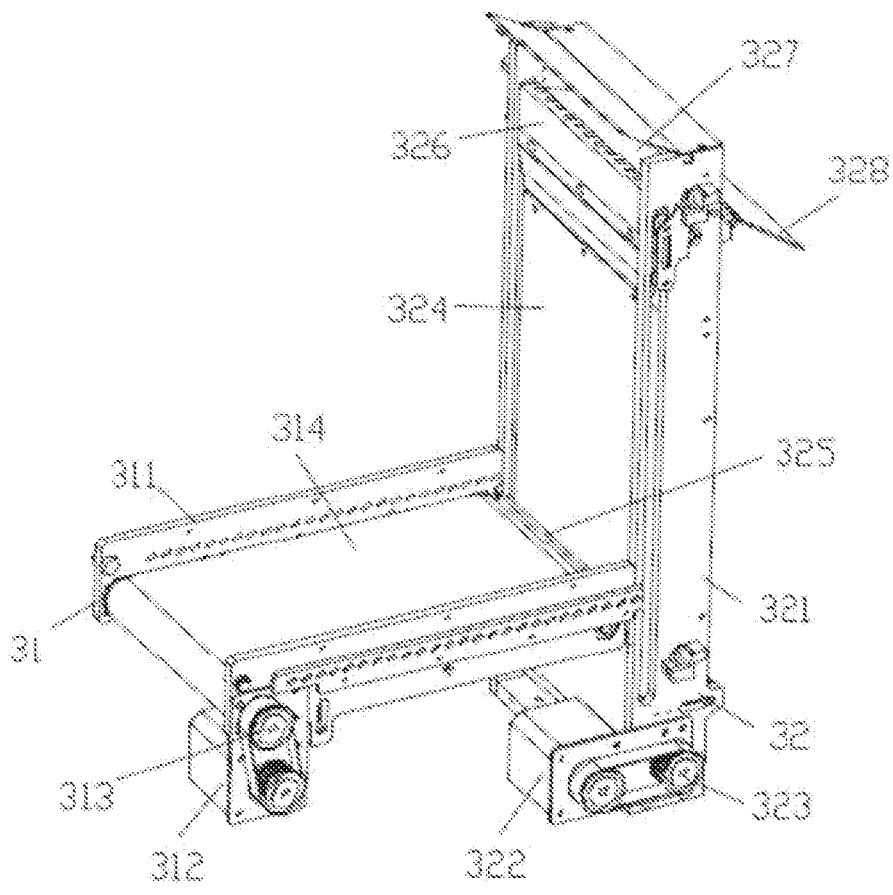
FIG. 4 is an internal schematic view of a centrifugal balancing tube mechanism according to an embodiment of the present disclosure.

Referring to FIG. 4, the centrifugal balancing tube mechanism 3 includes a balancing tube conveying mechanism 31, a balancing tube extracting mechanism 32, and a balancing tube hopper 33. The balancing tube hopper 33 is disposed on the balancing tube conveying mechanism 31, and the centrifugal balancing tube is placeable in the balancing tube hopper 33. The balancing tube conveying mechanism 31 and the balancing tube extracting mechanism 32 are parallelly arranged on the body frame 1. The balancing tube conveying mechanism 31 is configured to convey the centrifugal balancing tube in the balancing tube hopper 33 onto the balancing tube extracting mechanism 32. The balancing tube extracting mechanism 32 is configured to extract the centrifugal balancing tube conveyed by the balancing tube conveying mechanism 31 onto the test tube transporting mechanism 6.

The balancing tube conveying mechanism 31 includes a balancing tube conveying rack 311, a balancing tube conveying motor 312, a balancing tube transmission shaft 313, and a balancing tube conveying belt 314. The balancing tube conveying rack 311 is disposed across the body frame 1. The balancing tube transmission shaft 313 is disposed at two ends of the balancing tube conveying rack 311. The balancing tube conveying motor 312 is disposed at an end of the balancing tube conveying rack 311; and connected to the balancing tube transmission shaft 313 to drive the balancing tube transmission shaft 313. The balancing tube conveying belt 314 is disposed on the balancing tube transmission shaft 313 to convey the centrifugal balancing tube onto the balancing tube extracting mechanism 32.

The balancing tube extracting mechanism 32 includes a balancing tube extracting rack 321, a balancing tube extracting motor 322, a balancing tube extracting rotation shaft 323, a balancing tube extracting belt 324, a balancing tube transition block 325, a balancing tube extracting block 326, a balancing tube guide block 327, and a turning plate 328. The balancing tube extracting rack 321 is vertically disposed on the body frame 1. The balancing tube extracting rotation shaft 323 is disposed at two ends of the balancing tube extracting rack 321. The balancing tube extracting motor 322 is disposed at a lower end of the balancing tube extracting rack 321, and connected to the balancing tube extracting rotation shaft 323 to drive the balancing tube extracting rotation shaft 323. The balancing tube extracting belt 324 is disposed on the balancing tube extracting rotation shaft 323. The balancing tube transition block 325 is disposed on the balancing tube extracting rack 321 and located at a same level as the balancing tube conveying mechanism 31. The balancing tube extracting block 326 is disposed on the balancing tube extracting belt 324. The balancing tube guide block 327 and the turning plate 328 are parallelly arranged at an upper end of the vacuum tube extracting rack 321. The turning plate 328 is configured to guide the centrifugal balancing tube from the balancing tube guide block 327 to the test tube transporting mechanism 6 or guide the vacuum blood collection tube with incorrect label information sorted out by the sorting mechanism 4 into the collection box 7. The balancing tube extracting mechanism 32 is operated in a same manner as the vacuum tube extracting mechanism 22 expect that the centrifugal balancing tube falls into the test tube transporting mechanism 6 by the turning plate 328 when slipping from the balancing tube guide block 327, and the turning plate 328 can cooperate with the sorting mechanism 4 to guide the vacuum blood collection tube with the incorrect label information to be dropped into the collection box 7.

Figure 5:
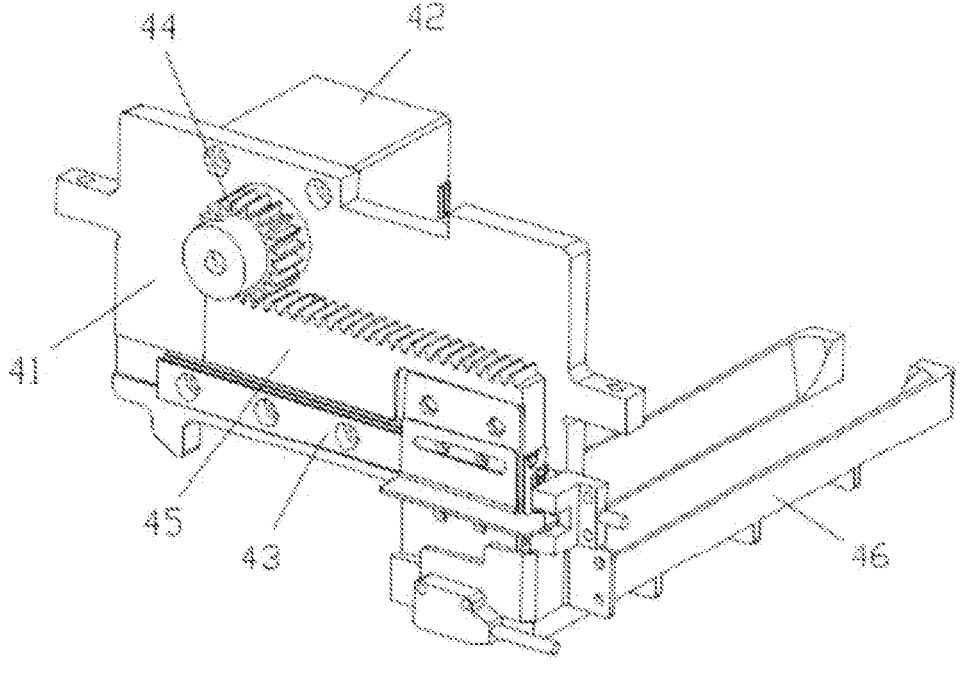
FIG. 5 is a schematic structural view of a sorting mechanism according to an embodiment of the present disclosure.

Referring to FIG. 5, the sorting mechanism 4 includes a sorting mounting plate 41, a sorting motor 42, a sorting slide rail module 43, a sorting transmission gear 44, a sorting transmission rack 45, and a sorting frame 46. The sorting mounting plate 41 is connected to the vacuum blood collection tube mechanism 2 and the centrifugal balancing tube mechanism 3 at two ends of the sorting mounting plate, respectively. Both the sorting motor 42 and the sorting slide rail module 43 are disposed on the sorting mounting plate 41. The sorting transmission gear 44 is connected to the sorting motor 42. Both the sorting transmission rack 45 and the sorting frame 46 are disposed on the sorting slide rail module 43. The sorting transmission rack 45 is engaged with the sorting transmission gear 44. The sorting motor 42 is configured to drive the sorting transmission gear 44 to drive the sorting transmission rack 45 and the sorting frame 46 to move along the sorting slide rail module 43. In operation, the sorting frame 46 is positioned directly above the scanning identification mechanism 5, and the vacuum blood collection tube slipping from the vacuum blood collection tube mechanism 2 would falls into the storing frame 46, i.e., on the scanning identification mechanism 5. When scanning result is obtained by the scanning identification mechanism 5, the vacuum blood collection tube with the correct label information is sorted to the test tube transporting mechanism 6 by the sorting frame 46, and the vacuum blood collection tube with the incorrect label information is driven to the turning plate by the sorting frame 46 and then slipped into the collection box 7. A movement of sorting frame 46 is realized by driving the sorting transmission gear 44 by the sorting motor 42 to drive the sorting transmission rack 45 to move along the sorting slide rail module 43, and the sorting frame 46 also moves to realize the sorting operation.

The present disclosure can identify and sort the vacuum blood collection tube through the sorting mechanism 4 and the scanning identification mechanism 5, and remove the vacuum blood collection tube with the incorrect label information. Thus, it is possible to avoid errors in subsequent operation. Through the centrifugal balancing tube mechanism 3, the centrifugal balancing tube can be matched with the vacuum blood collection tube entering the next process. Missing or over-matching will not occur through such fully automatic matching mode. The present disclosure provides an automatic device for pre-storing and centrifugal balancing for the automatic examination flow line, so that the automatic examination flow line can run smoothly under the unattended condition.

The above description is merely for the preferred embodiment of the present disclosure, and the scope of the present disclosure is not limited thereto. Any person skilled in the art can made equivalent substitutions or changes based on the technical solutions and the inventive concepts of the present disclosure within the scope of the present disclosure, and these equivalent substitutions or changes should be covered within the scope of the present disclosure.

What is claimed is:

1. A blood collection tube sorting and centrifugal balancing device, comprising a body frame, wherein:

a vacuum blood collection tube mechanism, a centrifugal balancing tube mechanism, a sorting mechanism, a scanning identification mechanism, a test tube transporting mechanism, and a collection box are arranged on the body frame;

the vacuum blood collection tube mechanism and the centrifugal balancing tube mechanism are parallelly arranged on an upper part of the body frame;

a vacuum blood collection tube is placeable into the vacuum blood collection tube mechanism, and the vacuum blood collection tube mechanism is configured to extract the vacuum blood collection tube onto the scanning identification mechanism;

a centrifugal balancing tube is placeable into the centrifugal balancing tube mechanism, and the centrifugal balancing tube mechanism is configured to extract the centrifugal balancing tube onto the test tube transporting mechanism;

the sorting mechanism, the scanning identification mechanism, and the test tube transporting mechanism are arranged between the vacuum blood collection tube mechanism and the centrifugal balancing tube mechanism;

the scanning identification mechanism and the test tube transporting mechanism are parallelly arranged below the sorting mechanism;

the scanning identification mechanism is connected to the vacuum blood collection tube mechanism and is configured to scan and identify a label of the vacuum blood collection tube extracted by the vacuum blood collection tube mechanism;

the sorting mechanism is connected to the vacuum blood collection tube mechanism and the centrifugal balancing tube mechanism at two ends of the sorting mechanism, respectively, and configured to sort the vacuum blood collection tube extracted onto the scanning identification mechanism by the vacuum blood collection tube mechanism;

the test tube transporting mechanism is connected to the centrifugal balancing tube mechanism, and configured to transport the vacuum blood collection tube with correct label information sorted out by the sorting mechanism and the centrifugal balancing tube extracted by the centrifugal balancing tube mechanism to a subsequent detection flow line for processing; and the collection box is disposed in a middle part of the body frame and located directly below the vacuum blood collection tube mechanism, and configured to collect the vacuum blood collection tube with incorrect label information sorted out by the sorting mechanism.

2. The blood collection tube sorting and centrifugal balancing device according to claim 1, wherein the vacuum blood collection tube mechanism comprises a vacuum tube conveying mechanism, a vacuum tube extraction mechanism, and a vacuum tube hopper, wherein:

the vacuum tube hopper is disposed on the vacuum tube conveying mechanism, and the vacuum blood collection tube is placeable into the vacuum tube hopper;

US 12,697,054 B2

11 the vacuum tube conveying mechanism and the vacuum tube extraction mechanism are parallelly arranged on the collection box;

the vacuum tube conveying mechanism is configured to convey the vacuum blood collection tube in the vacuum tube hopper to the vacuum tube extraction mechanism; and the vacuum tube extraction mechanism is configured to extract the vacuum blood collection tube conveyed by the vacuum tube conveying mechanism to the scanning identification mechanism.

3. The blood collection tube sorting and centrifugal balancing device according to claim 2, wherein the vacuum tube conveying mechanism comprises:

a vacuum tube conveying rack disposed transversely above the collection box;

a vacuum tube driving shaft disposed at two ends of the vacuum tube conveying rack;

a vacuum tube conveying motor disposed at one end of the vacuum tube conveying rack and connected to the vacuum tube driving shaft; and a vacuum tube conveying belt disposed on the vacuum tube driving shaft, wherein the vacuum tube conveying motor is configured to drive the vacuum tube driving shaft to drive the vacuum tube conveying belt to convey the vacuum blood collection tube onto the vacuum tube extracting mechanism.

4. The blood collection tube sorting and centrifugal balancing device according to claim 3, wherein the vacuum tube extracting mechanism comprises:

a vacuum tube extracting rack vertically disposed on the collection box;

a vacuum tube extracting rotation shaft disposed at two ends of the vacuum tube extracting rack;

a vacuum tube extracting motor disposed at a lower end of the vacuum tube extracting rack and connected to the vacuum tube extracting rotation shaft;

a vacuum tube extracting belt disposed on the vacuum tube extracting rotation shaft;

a vacuum tube transition block disposed on the vacuum tube extracting rack and located at a same level as the vacuum tube conveying mechanism;

a vacuum tube extracting block disposed on the vacuum tube extracting belt; and a vacuum tube guide block disposed at an upper end of the vacuum tube extracting rack, wherein the vacuum tube extracting motor is configured to drive the vacuum tube extracting rotation shaft to drive the vacuum tube extracting block to lift to extract the vacuum blood collection tube onto the scanning identification mechanism.

5. The blood collection tube sorting and centrifugal balancing device according to claim 4, wherein the scanning identification mechanism comprises:

a scanning rack disposed on the vacuum tube extracting rack;

scanning dual rollers disposed on a top of the scanning rack;

a scanning motor disposed on the scanning rack, and connected to the scanning dual rollers to drive the scanning dual rollers; and a scanner disposed on a bottom of the scanning rack and corresponding to a gap between the scanning dual rollers.

6. The blood collection tube sorting and centrifugal balancing device according to claim 1, wherein the test tube transporting mechanism comprises:

a transporting rack connected to the centrifugal balancing tube mechanism;

a transporting driving wheel disposed at two ends of the transporting rack;

a transporting motor disposed at one end of the transporting rack, and connected to the transporting driving wheel to drive the transporting driving wheel;

a transporting belt disposed on the transporting driving wheel to receive and transport the vacuum blood collection tube conveyed from the sorting mechanism or the centrifugal balancing tube conveyed from the centrifugal balancing tube mechanism; and a transporting guide block disposed at one end of the transporting rack and configured to accurately place the vacuum blood collection tube or the centrifugal balancing tube on the transporting belt onto the subsequent detection flow line.

7. The blood collection tube sorting and centrifugal balancing device according to claim 6, wherein the centrifugal balancing tube mechanism comprises a balancing tube conveying mechanism, a balancing tube extracting mechanism, and a balancing tube hopper, wherein:

the balancing tube hopper is disposed on the balancing tube conveying mechanism, and the centrifugal balancing tube is placeable in the balancing tube hopper;

the balancing tube conveying mechanism and the balancing tube extracting mechanism are parallelly arranged on the body frame;

the balancing tube conveying mechanism is configured to convey the centrifugal balancing tube in the balancing tube hopper onto the balancing tube extracting mechanism; and the balancing tube extracting mechanism is configured to extract the centrifugal balancing tube conveyed by the balancing tube conveying mechanism onto the test tube transporting mechanism.

8. The blood collection tube sorting and centrifugal balancing device according to claim 7, wherein the balancing tube conveying mechanism comprises:

a balancing tube conveying rack disposed across the body frame;

a balancing tube transmission shaft disposed at two ends of the balancing tube conveying rack, a balancing tube conveying motor disposed at one end of the balancing tube conveying rack, and connected to the balancing tube transmission shaft to drive the balancing tube transmission shaft; and a balancing tube conveying belt disposed on the balancing tube transmission shaft to convey the centrifugal balancing tube to the balancing tube extracting mechanism.

9. The blood collection tube sorting and centrifugal balancing device according to claim 8, wherein the balancing tube extracting mechanism comprises:

a balancing tube extracting rack vertically disposed on the body frame;

a balancing tube extracting rotation shaft disposed at two ends of the balancing tube extracting rack;

a balancing tube extracting motor disposed at a lower end of the balancing tube extracting rack, and connected to the balancing tube extracting rotation shaft to drive the balancing tube extracting rotation shaft;

a balancing tube extracting belt disposed on the balancing tube extracting rotation shaft;

a balancing tube transition block disposed on the balancing tube extracting rack and located at a same level as the balancing tube conveying mechanism;

a balancing tube extracting block disposed on the balancing tube extracting belt;

a balancing tube guide block; and a turning plate, the balancing tube guide block and the turning plate being parallelly arranged at an upper end of the vacuum tube extracting rack, and the turning plate being configured to guide the centrifugal balancing tube from the balancing tube guide block to the test tube transporting mechanism or guide the vacuum blood collection tube with incorrect label information sorted out by the sorting mechanism to the collection box.

10. The blood collection tube sorting and centrifugal balancing device according to claim 9, wherein the sorting mechanism comprises:

a sorting mounting plate connected to the vacuum blood collection tube mechanism and the centrifugal balancing tube mechanism at two ends of the sorting mounting plate, respectively, a sorting motor disposed on the sorting mounting plate;

a sorting slide rail module disposed on the sorting mounting plate;

a sorting transmission gear connected to the sorting motor;

a sorting transmission rack disposed on the sorting slide rail module and engaged with the sorting transmission gear; and a sorting frame disposed on the sorting slide rail module, wherein the sorting motor is configured to drive the sorting transmission gear to drive the sorting transmission rack and the sorting frame to move along the sorting slide rail module.

* * * * *